United States Patent [19]

Keime

[11] Patent Number: 4,673,392
[45] Date of Patent: Jun. 16, 1987

[54] PORTABLE SELF-CONTAINED INJECTOR FOR PERFUSIONS, PARTICULARLY IN THE CASE OF ROAD ACCIDENT VICTIMS

[76] Inventor: Bernard M. Keime, 26, Rue des Begonias, 54000 Nancy, France

[21] Appl. No.: 783,200

[22] Filed: Oct. 2, 1985

[51] Int. Cl.⁴ .............................................. A61M 5/00
[52] U.S. Cl. ........................... 604/141; 128/DIG. 12
[58] Field of Search ...................... 604/140, 141, 118; 128/DIG. 12

[56] References Cited

U.S. PATENT DOCUMENTS

| | | | |
|---|---|---|---|
| 2,842,123 | 7/1958 | Rundhaug | 604/141 |
| 3,640,277 | 2/1972 | Adelberg | 604/118 X |
| 3,895,741 | 7/1975 | Nugent | 604/141 X |
| 4,539,005 | 9/1985 | Greenblatt | 604/141 |

Primary Examiner—Dalton L. Truluck
Attorney, Agent, or Firm—Erwin S. Teltscher

[57] ABSTRACT

Portable self-contained injector for perfusions.

Injector characterized by the association of a transparent fluidtight casing (1) and a neutral liquefied gas compression assembly (18), the said casing containing a flexible bag (2) containing liquid which is to be perfused and having a removable plate on its upper face and provided with a fluidtight connection with the flow line and safety elements.

This invention is useful for manufacturers of portable medical equipment and in particular manufacturers of emergency treatment equipment.

5 Claims, 4 Drawing Figures

PORTABLE SELF-CONTAINED INJECTOR FOR PERFUSIONS, PARTICULARLY IN THE CASE OF ROAD ACCIDENT VICTIMS

BACKGROUND OF THE INVENTION

The present invention relates to a portable self-contained injector for carrying out perfusions, particularly in the case of road accident victims.

The injection of a biological liquid, an act referred to as a perfusion, is currently still carried out by means of a phial containing the liquid to be injected, suspended from the end of a support about 1 meter above the patient.

The liquid empties by gravity at a rate of flow which can be regulated by what is known as a drop-by-drop device or 'drip' which reduces the rate of flow by restriction or compression of the flexible pipe carrying the liquid which is to be injected.

Although this equipment is used in a hospital room, it is however bulky, difficult to move, clumsy and slow to set up and therefore not readily adapted to the rendering of assistance in the field as in the majority of cases of victims of catastrophes or road accidents.

Moreover, doctors realise the basic usefulness of perfusions of biological liquids, particularly water. Indeed, the loss of blood, the emotional shock and the conditions of sanitary transportation to the place of treatment do give rise to systematic dehydration requiring a direct input of water, drinks being inadequate.

SUMMARY OF THE INVENTION

The self-contained and portable apparatus according to the invention, by reason of its convenience and simplicity of use, is aimed at providing a precious aid and a new facility available to treatment teams in catastrophes and road accidents and work accidents, teams which have to encounter all kinds of difficulties and in most cases have to treat numerous injured persons at one and the same time.

Initial care and attention has been demonstrated as determining the vital or functional prognosis of victims and to be effective must therefore employ reliable and rapidly implemented equipment.

The apparatus according to the invention does not require any skill in use. It is easily and quickly positioned. Carried by the injured person, there is no longer any overhead supporting structure nor connecting line, causes of the main hindrance in handling and transporting the patient.

To this end, the self-contained and portable injector for perfusion according to the invention is composed of a fluidtight casing enclosing the flexible bag containing the physiological liquid. One of the walls of the casing is removable and incorporates the main monitoring and safety elements: a decompression valve, a safety valve and a passage for the flexible feed line, at the end of which is an injection or perfusion needle.

The casing communicates via an orifice with a compression assembly comprising a neutral liquid gas cartridge and an injector, followed by an element for regulating and controlling the pressure. The casing has straps by which it is fixed to one of the victim's limbs.

Apart from the main advantages already mentioned above, the following additional advantages can be mentioned:

lightness and small dimensions permitting of easy usage without discomfort for the injured person or patient; simplicity of the constituent parts guaranteeing a low prime cost;

ensurance of a constant rate of flow.

BRIEF DESCRIPTION OF THE DRAWING

The technical characteristics of the invention and other advantages are set forth in the ensuing description which is given by way of non-limitative example, relative to an embodiment illustrated in the accompanying drawings, in which.

DESCRIPTION OF THE PREFERRED EMBODIMENT

Figure 1:
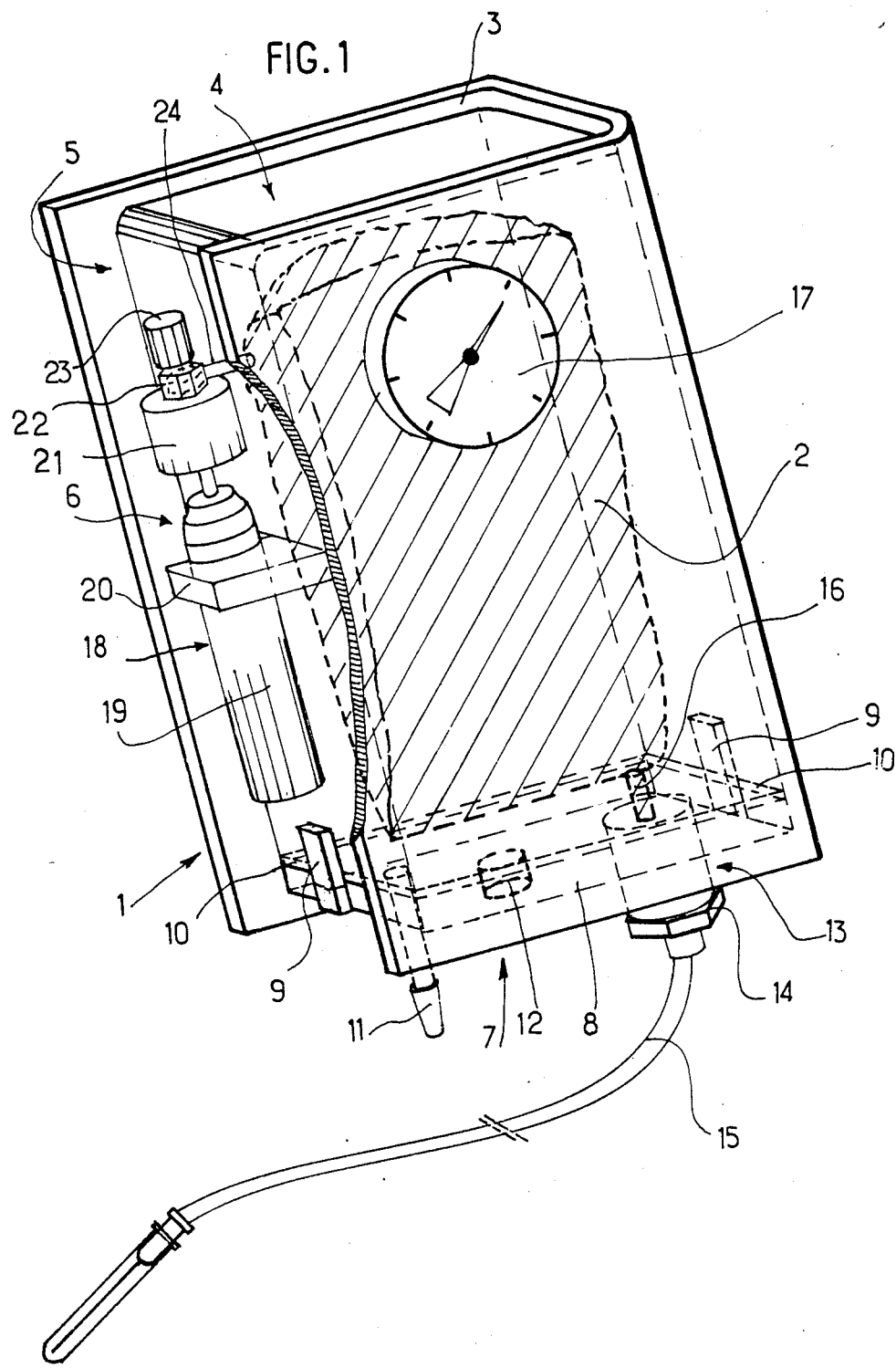
FIG. 1 is a perspective view in an upside-down position of the perfusion injector according to the invention.
Figure 2:
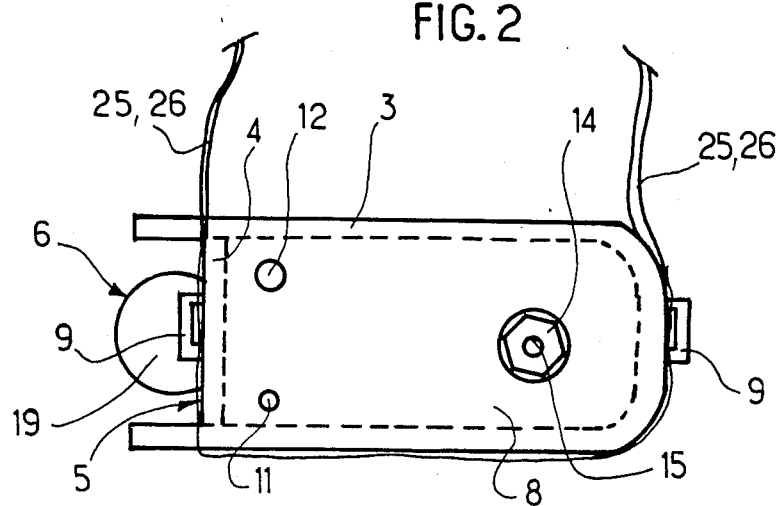
FIG. 2 is a plan view of the upper face.
Figure 3:
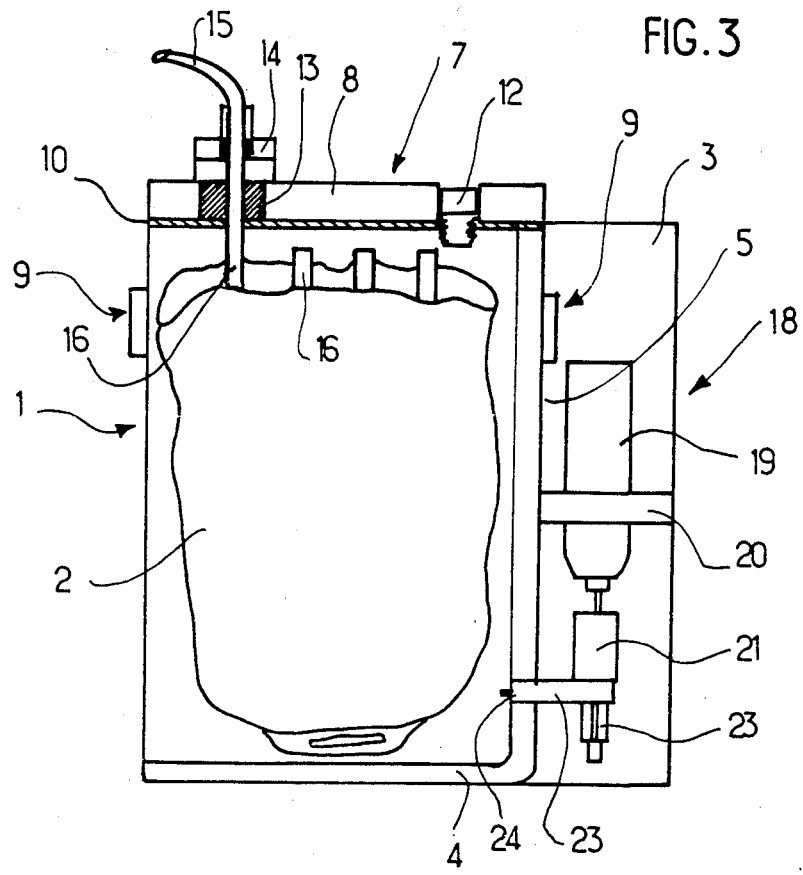
FIG. 3 is a view in longitudinal section through the plan.
Figure 4:
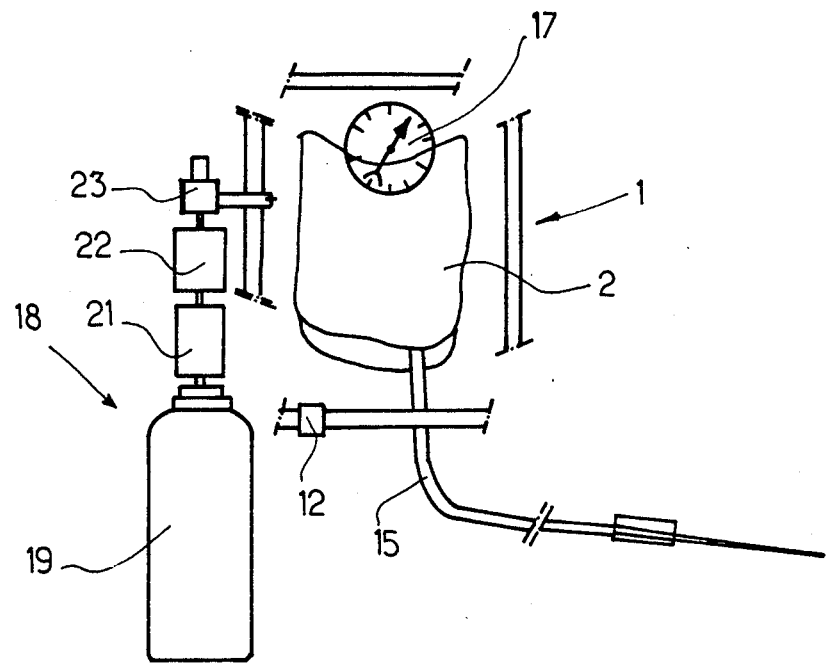
FIG. 4 is a diagrammatic view illustrating the succession of functions which make it possible for the perfusion to be carried out in an entirely safe manner.

A basic embodiment will be described hereinafter but it will be appreciated that various simple variations and secondary modifications will in no way alter the invention. Similarly, variations in choice and use of materials will not constitute any supplementary inventive element and consequently will not depart from the framework of the present protection.

The injector is composed of a fluidtight casing 1 of for example parallelepiped form and of dimensions suited to those of the flexible bag 2 containing the physiological liquid to be injected. The casing will preferably be of transparent plastic material in order to permit immediate visual monitoring of the condition of the inner bag.

The casing 1 is for example but not necessarily formed from a sheet of transparent plastic material forming a U-shaped envelope 3 bounding between its two arms an open rectangular space. The space is enclosed at the sides by an L-shaped closure member 4 which is bent over and glued onto the inside faces of the walls of the envelope 3.

These latter extend beyond the side face 5 constituted by the long side of the closure member 4, to form an outer lateral space 6 protected from shocks by the extensions of the wings of the envelope 3. This space will be used for technical purposes and will be referred to hereinafter as the open-sided chamber 6.

At its upper side 7, the casing 1 is closed by a removable front plate 8 which is attached to the abutting edges of the envelope 3 by means of rapid fastenings such as 9. Sealing tightness is ensured by the interposition of a gasket 10, for example a flat gasket or one of any other suitable profile.

The front plate 8 on the upper face 7 comprises, screwed or fixed in appropriate manner into its body, a decompression valve 11 and a safety valve 12 calibrated or regulated to a limited pressure beyond which satisfactory operating conditions are not longer guaranteed.

The front plate 8 also has a fluidtight passage 13 fitted with a gasket 14 permitting fluidtight leadthrough of the flexible flow line 15 at the end of which is an injection or perfusion needle. The other end of the pipe is mounted originally and with no possibility of separation, on one of the outlet nozzles 16 of the flexible bag 2.

On one of its faces, the casing 1 comprises a pressure gauge 17 indicating the pressure prevailing in its inner space.

In the open-sided chamber 6 extending along one side of the casing is housed a compression assembly 18 supplied by a pressurised neutral gas cartridge 19 which is in the liquid state and which is maintained therein by one or two cross-members such as 20..

The compression assembly 18 extends to by an injection module 21 which receives the gas at the pressure in the cartridge, a relief valve 22 and flow regulator 23 adapted for manual control, the outlet 24 of which discharges into the casing after passing therethrough in fluidtight manner by adhesion or interposition of a circular seal or any other means.

The presence of the pressure relief valve 22 is not vital because the flow regulator 23 can fulfil the same function. However, it does make it possible to obtain greater facility and precision of pressure adjustment.

Two straps 25 and 26 are provided for fixing the casing on one of the patient's limbs. In its commercial version, the injector will have these straps attached to the casing or threaded through slots so that the casing can be strapped on at two levels.

Preferably chosen as the gas will be dischlorodifluoromethane R 12 known under the designation "freon" or mixtures derived from existing fluorinated chlorides. This gas is packed in small-capacity cartridges which are easily housed in the open-sided chamber 6. The containers can be disposed of after use. The capacity proves adequate for complete evacuation of the bags 2 currently available on the market, in other words 50 ml of liquid for perfusion purposes.

These cartridges have the particular feature of containing liquid gas inside them.

The various phases of operation of the slow perfusion injector according to the invention will now be explained.

In order to use the injector according to the invention, the following procedure should be adopted. With the flexible bag 2 fitted inside the case 1 with its flow line 15, the latter is passed through the lid, through the seal, after which the casing is closed again by means of the rapid fasteners 9.

The flexible bag 2 is placed in position in the casing which is closed again. The inert gas cartridge is changed and pushed fully into its housing. The appliance is fixed to a conveniently near limb of the patient, generally the thigh, by using the straps 25 and 26. The perfusion needle is introduced into the patient's skin. The gas cartridge is changed if the change has been previously forgotten.

The next stage is to build up pressure. To do this, the gas is released by acting on the regulator 23 and the pressure is progressively shut down to about 10 millibars beyond the chosen pressure, after which it is stabilised at the final level.

If it is exceeded, when the pressure is applied or if the pressure is accidentally overshot, it is sufficient to drain off the excess through the decompression valve and then to readjust the pressure as indicated hereinabove.

The liquid is evacuated from the bag as soon as the pressure threshold is exceeded, the threshold being determined by the characteristics of the apparatus.

The gas reserve proves adequate to evacuate all the liquid contents of the bag 2. When the operation is completed, the liquid having been completely injected, the gas continues to fill the casing and the pressure in this latter rises with no danger by virtue of the safety valve and the reserve of gas in the cartridge, which arrives at its limit of use.

The apparatus is removed from the patient before it is opened so that it can be restored to operating condition by decompression, replacement of the gas cartridge and of the flexible bag 2.

The invention above cannot be confined just to the means, materials and elements described, all their equivalence amd all their alternatives, additions and other modifications which involve no inventive contribution being on the contary entirely within its framework.

I claim:

1. A self-contained portable injector for perfusing a liquid into the body of a patient, and adapted to be carried by the patient, comprising in combination
   a transparent enclosure,
   a divider subdividing said enclosure into a first chamber having an open side, and into a second chamber,
   said enclosure including
   a U-shaped envelope formed with two legs and a center member joining said legs, an L-shaped bracket fitting the interior of said U-shaped envelope, a shorter arm of said L-shaped bracket having a length smaller than the length of each leg of said U-shaped envelope, thereby creating said first chamber with said open side,
   pressure-exerting means disposed in said first chamber and communicating with said second chamber for creating a controllable gas pressure in said second enclosure,
   cross-member means secured to said enclosure, said pressure-exerting means being mounted on said cross-member means,
   a flexible pouch disposed in said second enclosure and adapted to contain said liquid, said gas pressure acting on said flexible pouch,
   at least one outlet nozzle commnicating with said flexible pouch, and being adapted to inject said fluid into the patient, and
   flexible conduit means connected to said outlet nozzle and adapted to attach said enclosure to the patient.

2. The portable injector as claimed in claim 1, wherein said pressure-exerting means includes a replaceable cartridge adapted to hold an inert gas in a liquified state, and a pressurizing unit communicating with said cartridge.

3. The portable injector as claimed in claim 1, further comprising a gas injection module communicating with an outlet said pressure-exerting means, a gas-pressure expander communicating with said gas injection module, and a manually controlled gas flow regulator communicating with said gas-pressure expander.

4. The portable injector as claimed in claim 1, wherein said enclosure includes a cover on a side opposite said shorter arm of said L-shaped bracket, and being releasably attached to said enclosure, said cover being fitted with a decompression valve, and a safety release valve actuatable at a predetermined gas pressure, and being formed with a fluid-tight lead-through accomodating said flexible conduit means.

5. The portable injector as claimed in claim 4, further comprising a gasket on an inner side of said cover, pressure indicating means mounted on said second chamber so as to be visible from the exterior thereof, and patient attachment means secured to said enclosure.

* * * * *